United States Patent
Gattinoni et al.

(10) Patent No.: US 9,775,581 B2
(45) Date of Patent: Oct. 3, 2017

(54) METHOD FOR DETERMINING INHOMOGENEITY IN ANIMAL TISSUE AND EQUIPMENT TO IMPLEMENT IT

(71) Applicant: FONDAZIONE IRCCS CA' GRANDA OSPEDALE MAGGIORE POLICLINICO, Milan (IT)

(72) Inventors: Luciano Gattinoni, Milan (IT); Paolo Cadringher, Monza (IT); Massimo Cressoni, Monza (IT)

(73) Assignee: FONDAZIONE IRCCS CA' GRANDA OSPEDALE MAGGIORE POLICLINICO, Milan (IT)

( * ) Notice: Subject to any disclaimer, the term of this patent is extended or adjusted under 35 U.S.C. 154(b) by 508 days.

(21) Appl. No.: 14/364,551

(22) PCT Filed: Dec. 11, 2012

(86) PCT No.: PCT/IB2012/057172
§ 371 (c)(1),
(2) Date: Jun. 11, 2014

(87) PCT Pub. No.: WO2013/088336
PCT Pub. Date: Jun. 20, 2013

(65) Prior Publication Data
US 2014/0343414 A1    Nov. 20, 2014

(30) Foreign Application Priority Data

Dec. 13, 2011   (IT) .............................. CO2011A0062

(51) Int. Cl.
*A61B 6/00*   (2006.01)
*A61B 6/03*   (2006.01)
(Continued)

(52) U.S. Cl.
CPC ............ *A61B 6/5217* (2013.01); *A61B 6/032* (2013.01); *A61B 6/50* (2013.01); *G06T 7/0012* (2013.01);
(Continued)

(58) Field of Classification Search
CPC ......... A61B 6/5217; A61B 6/032; A61B 6/50; G06T 7/0012; G06T 7/401; G06T 2207/30061
(Continued)

(56) References Cited

PUBLICATIONS

Gattinoni, L., "Mechanical ventilation in ALI/ARDS patients: do any harmful thresholds really exist?" Symposium on Intensive Care, NL, Apr. 15, 2010, PowerPoint presentation.*
(Continued)

*Primary Examiner* — Long V Le
*Assistant Examiner* — Katherine McDonald
(74) *Attorney, Agent, or Firm* — Abelman, Frayne & Schwab (57) ABSTRACT

The present invention relates to a method for determining inhomogeneity in a portion of animal tissue, which provides for the arrangement beforehand of a 3-dimensional density map of said portion of tissue; the map is obtained by means of computed tomography and therefore is formed by a plurality of voxels (VX); for each voxel (VX) of the map, respectively considered as the central voxel (VXC), the following steps are carried out:—determining a space (CC) surrounding the central voxel (VXC) and containing a group of peripheral voxels (VXP),—for each peripheral voxel (VXP) of the group, calculating a value proportional to the ratio or the difference between the density of the peripheral voxel (VXP) and the density of the central voxel (VXC), thus obtaining a plurality of values,—calculating the maximum value and/or the minimum value and/or the average value and/or a statistical partitioning value of these values, thus obtaining a local indicator of inhomogeneity in the animal tissue in correspondence to the central voxel (VXC). Such method can advantageously be implemented in an equipment.

9 Claims, 2 Drawing Sheets

(51) Int. Cl.
*G06T 7/00* (2017.01)
*G06T 7/41* (2017.01)

(52) U.S. Cl.
CPC ...... *G06T 7/41* (2017.01); *G06T 2207/30061* (2013.01)

(58) Field of Classification Search
USPC ........................................................ 600/427
See application file for complete search history.

(56) References Cited

PUBLICATIONS

Jere Mead et al., "Stress distribution in lungs: a model of pulmonary elasticity," Journal of Applied Physiology, 28:5:596-608 (May 1970).

J. Mead et al., "Stress distribution in lungs: a model of pulmonary elasticity," J. Appl. Physiol., 1970, 28(5), p. 596-608 (13 pages).

M. Cressoni et al., "Lung Inhomogeneity in Patients with Acute Respiratory Distress Syndrome," Am. J. Respir. Crit. Care Med., 2014, 189(2): p. 149-58 (10 pages).

M. Cressoni et al., "Lung Inhomogeneities and Time Course of Ventilator-induced Mechanical Injuries," Anesthesiology, 2015, 123(3), p. 618-27 (10 pages).

M. Cressoni et al., "Lung inhomogeneities, inflation and [18F]2-fluoro-2-deoxy-D-glucose uptake rate in acute respiratory distress syndrome," Eur. Respir. J., 2016. 47(1), p. 233-42 (10 pages).

L. Gattinoni et al., "Ventilator-related causes of lung injury: the mechanical power," Intensive Care Med., 2016. 42(10), p. 1567-75 (9 pages).

M. Cressoni et al., Mechanical Power and Development of Ventilator-induced Lung Injury. Anesthesiology, 2016. 124(5), p. 1100-8 (9 pages).

* cited by examiner

METHOD FOR DETERMINING INHOMOGENEITY IN ANIMAL TISSUE AND EQUIPMENT TO IMPLEMENT IT

RELATED APPLICATIONS

This application is a §371 of PCT/IB2012/057172 filed Dec. 11, 2012, and claims priority from Italian Patent Application No. CO2011A000062 filed Dec. 13, 2011, both incorporated by reference in their entirety.

FIELD OF THE INVENTION

The present invention relates to a method for determining inhomogeneity in animal tissue and to an equipment implementing it.

More in particular, the present invention has been devised and finds a certainly advantageous application for the human tissue, especially the human lung tissue.

PRIOR ART

The present invention results from the problems related to the mechanical ventilation of patients. Mechanical ventilation at high pressures/volumes may seriously damage the lungs (edema diffused to the whole lung tissue), as experience teaches; as it seems, the lung damage caused by mechanical ventilation is proportional to the pressures/volumes used.

The behavior of the lung, as elastic body, may be better described in bioengineering terms as "stress" and "strain"; "strain" is the extension of the lung fibers starting from the rest position thereof; "stress" is the corresponding pressure applied to the lung fibers; these two elements are linked to each other.

When a certain "stress/strain" threshold is exceeded, mechanical ventilation becomes harmful for the lung fibers.

However, considering the mechanical ventilation treatments, the damages occurred on the basis of the pressures and volumes used cannot always be justified.

SUMMARY OF THE INVENTION

The Inventors have assumed that, in diseased lungs, there are "local multipliers" (also called "stress raisers") of pressure.

This hypothesis of the Inventors also results from the research activities of Jere Mead, Tamotsu Takishima and David Leith; their article, "Stress distribution in lungs: a model of pulmonary elasticity", published in May 1970 on the Journal of Applied Physiology (Vol. 28, No. 5), summarizes their studies and experiments. The activity of these people was essentially theoretical but also led to the production of mechanical models; on the other hand, it does not appear that they carried out experiments on the lung tissue.

Thereafter, the Inventors carried out studies on the lung tissue of both healthy individuals, and of individuals suffering from moderate ARDS (Acute Respiratory Distress Syndrome) and individuals suffering from severe ARDS. The result of these studies is summarized in the presentation "Mechanical ventilation in ALI/ARDS patients: do any harmful thresholds really exist?" made by Prof. Gattinoni (the main Inventor) in Utrecht in 2010. According to this presentation (see from page 16 on), in healthy individuals (see in particular the histogram on page 19), most voxels related to the lung tissue have a "gas fraction" in the range 0.7-0.9 and a "gas ratio" in the range 1.0-1.5; in not very sick individuals (see in particular the histogram on page 21), most voxels related to the lung tissue have a "gas fraction" in the range 0.5-0.9 and a "gas ratio" in the range 1.0-1.5; in not very sick individuals (see in particular the histogram on page 23), most voxels related to the lung tissue have a "gas fraction" in the range 0.2-0.5 and a "gas ratio" in the range 1.0-2.5. The meaning of "gas fraction" and "gas ratio", in detail of "weighted gas ratio", is explained on page 16 of the presentation; the "gas fraction" corresponds to the gas percentage in a lung tissue unit of an expanded lung; the "weighted gas ratio" is an index of inhomogeneity between two portions of tissue (one, when the two portions of tissue are equal and homogeneous) and the "gas ratio" related to a lung tissue unit is the sum of the "weighted gas ratios" related to the surrounding tissue.

The Inventors have then deemed that the "local multipliers" consist of inhomogeneities at the lung tissue level and that it is very important to take into account the fact that they are "local": in fact, even in the presence of a safe "global strain" level, lung regions are subjected to a harmful "local strain" due to local inhomogeneities of the lung tissue; this should be taken into account in case of mechanical ventilation and above all, for patients with diseased lungs.

Hence the need to assess the lung inhomogeneity in a quantitative manner. Based on such assessment carried out on the lung tissue of a patient it will be possible to quantify the pressure multipliers present in the lung and provide information about the mechanical ventilation safety for such patient.

The general object of the present invention is to provide a method for determining inhomogeneity in animal tissue which is effective and possibly, flexible.

A first more specific object of the present invention is to provide a method for determining inhomogeneity in animal tissue which is capable of providing quantitative information (i.e. indicating the inhomogeneity extent).

A second more specific object of the present invention is to provide a method for determining inhomogeneity in animal tissue which is capable of providing punctual information (i.e. indicating the inhomogeneity point or points).

A third more specific object of the present invention is to provide a method for determining inhomogeneity in animal tissue which is based on methods and/or equipments already existing and working, so that it is easily and quickly implemented in the practice.

A fourth object of the present invention is to provide a method for determining inhomogeneity in animal tissue which is particularly suitable and effective for the human lung tissue.

These and other objects are achieved thanks to the method having the features described in the annexed claims, which form an integral part of the present description.

The idea at the basis of the present invention is to determine the inhomogeneity in a portion of animal tissue using computed tomography; i.e. the first step to make is arranging beforehand a 3-dimensional density map of the portion of tissue obtained by means of computed tomography; the map is therefore formed by a plurality of "voxels".

In general, for each voxel of the map, respectively considered as the central voxel, the following steps are carried out:

identifying a space surrounding the central voxel and containing a group of peripheral voxels, for each peripheral voxel of the group, calculating a value proportional to the ratio or the difference between the density of the peripheral voxel and the density of the central voxel, thus obtaining a plurality of values, calculating the maximum value and/or the minimum value and/or the average value and/or a statistical partitioning value of these values, thus obtaining a local indicator of inhomogeneity in the portion of animal tissue in correspondence to the central voxel.

A threedimensional inhomogeneity map of the portion of animal tissue is thus obtained, which may for example be the whole lung tissue of an individual. It is therefore understood that the Inventors have made a further step compared to the ideas expressed in their presentation of 2010. In fact, while that presentation regarded the overall inhomogeneity of a large portion of tissue (see for example the histograms included in the presentation) as significant, according to the present invention, the local inhomogeneity is regarded as significant and is precisely quantified; in particular, A) only a predetermined small neighborhood (called "space" in the above steps) of a voxel of the lung tissue is considered, and B) the inhomogeneity directionality is taken into account (in the above steps, reference is made to "the maximum value and/or the minimum value and/or the average value and/or a statistical partition value").

Said space is preferably a sphere centered on said central voxel; more preferably, the sphere is hollow so as to exclude said central voxel and a neighborhood thereof.

The smaller radius of said sphere may be comprised between 0.0 mm (non hollow sphere) and 8.9 mm, in particular between 0.0 mm (non-hollow sphere) and 7.1 mm, more in particular between 2.2 mm and 5.3 mm.

The larger radius (which simply corresponds to the radius, in case of non hollow sphere) of said sphere may be comprised between 0.4 mm and 13.4 mm, in particular between 1.1 mm and 10.6 mm, more in particular between 3.3 mm and 8.8 mm.

The thickness of said sphere may be comprised between 0.4 mm and 4.5 mm, in particular between 1.1 mm and 3.5 mm.

The above values have been selected based on a reference dimension, i.e. that of the radius of the medium lung acinus in different conditions of the human lung, as will appear more clearly from the detailed description.

Said 3-dimensional map may derive from a threedimensional original map produced by a standard computed tomography equipment and then spatially filtered by means of a spatial low-pass filter strongly attenuating spatial frequencies higher than a predetermined frequency corresponding to the reciprocal for a predetermined length.

Said predetermined length may be comprised in the range from 2.2 mm to 3.5 mm.

Said predetermined length may be equal to about the radius of the medium lung acinus in conditions TLC/4 or TLC/3 or TLC/2 or TLC (TLC="Total Lung Capacity"); it is noted that the radius of the medium lung acinus in conditions TLC/4 corresponds to about the radius of the medium lung acinus in conditions FRC (FRC="Functional Residual Capacity").

The transfer function of said spatial low-pass filter may be decreasing monotone, preferably a Gaussian function.

According to a particular and advantageous embodiment, for each voxel of said map, respectively considered as the central voxel, the following steps are carried out:
A) calculating the "gas fraction" of said central voxel,
B) identifying a space shaped as a hollow sphere surrounding said central voxel and containing a group of peripheral voxels,
C) for each peripheral voxel of said group, calculating a value corresponding to the ratio between the "gas fraction" of said peripheral voxel and the "gas fraction" of said central voxel, thus obtaining a plurality of values,
D) calculating the maximum value among said values, thus obtaining a local indicator of inhomogeneity of said portion of animal tissue in correspondence to said central voxel.

In this example, the densities of said 3-dimensional map of said portion of tissue are advantageously saturated in a range comprised between a minimum value, in particular −1000, and a maximum value, in particular −100 or −10; such operation is typically made after an optional spatial filtering.

In this example, in said step D, the local indicators of inhomogeneity are advantageously saturated to a minimum value, in particular 1.

In this example, the density values of said 3-dimensional map of said portion of tissue are advantageously considered only if lower than a predetermined value, in particular +10 or +100; such operation is typically made after an optional spatial filtering.

Said portion of animal tissue corresponds to a whole lung, in particular a whole human lung.

A global indicator of inhomogeneity may be obtained from said local indicator of inhomogeneity of all voxels of said portion of animal tissue.

An overall inhomogeneity level may be noted if for a predetermined percentage of said voxels, said local indicator of inhomogeneity exceeds a predetermined threshold.

A hazard level may be noted if for a predetermined percentage of said voxels, the product between the transpulmonary pressure during a mechanical ventilation treatment and said local indicator of inhomogeneity raised to a predetermined power exceeds a predetermined threshold.

Said predetermined power advantageously is $2/3$, an exponent that makes a proportion of the area to the volume in an isomorphous expansion.

Said predetermined percentage may be about 5%.

Said predetermined threshold may be about 20 cmH2O.

The above method (or equivalent variants thereof) may be implemented thanks to a computer program; such a program may be loaded and executed, for example, by a computer built in a standard computed tomography equipment.

According to a further aspect, the present invention also relates to an equipment implementing such method.

Such equipment may comprise memory means storing the above computer program. Typically, said means comprises one or more internally stored computer programs.

BRIEF DESCRIPTION OF THE FIGURES

The technical features of the present invention as well as the advantages thereof will appear more clearly from the following description, made with reference to the annexed drawings, wherein.

DETAILED DESCRIPTION OF THE INVENTION

Both such description and such drawings are to be deemed for illustration purpose only and therefore nonlimiting; therefore, the present invention may be implemented according to other and different embodiments.

As already said, the method according to the present invention starts from a threedimensional density map of a portion of tissue; conceptually, the method assumes that the map refers to a portion of tissue that may be considered as uniform; for example and typically, the tissue and the relevant map of a whole human lung.

The threedimensional density map is obtained by the known computed tomography technique and is therefore formed by a plurality of "voxels" (or "volumetric picture element", it is a volume element representing a signal intensity value in a 3-dimensional space).

Figure 1:
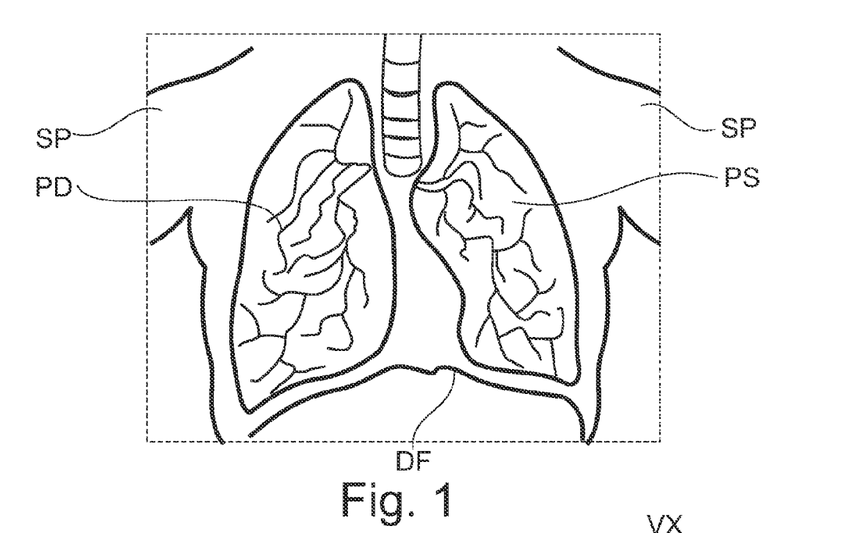
FIG. 1 schematically shows the human lungs in a chest.

For example, a whole human chest between the shoulders SP and diaphragm DF and thus, the two lungs PD and PS, may be scanned by computed tomography as shown in FIG. 1. However, in order to implement the method according to the present invention it is necessary to delimit the volume of uniform tissue in the map, for example and typically, that of a whole lung. Such delimitation or contouring operation may be made manually by an operator or semi-automatically or automatically by a computer program that processes the original threedimensional map.

It should be noted that the computed tomography equipment currently manufactured and marketed provide high-resolution threedimensional density maps to allow the details to be well displayed. The method according to the present invention requires a threedimensional density map with a predetermined and narrow "spatial band" (in other words, with a predetermined and low maximum spatial frequency); a narrow band 3-dimensional may correspond to a low-resolution threedimensional map. Therefore, if the method according to the present invention is implemented using commercial computed tomography equipment, a spatial filtering will be required beforehand, as will appear more clearly hereinafter.

The same processing is repeated for each voxel of the 3-dimensional density map of interest. It should be noted that the voxels in the vicinity of the of the limit or contour of the portion of tissue of interest must be processed in a slightly different manner to keep into account the conditions at the contour; for these voxels, the peripheral voxels falling beyond the limit or contour of the portion of tissue are ignored.

The process will now be described with reference to FIG. 2 which shows (on one plane only) one of voxels VXL of the 3-dimensional map considered as if it were a "central voxel" VXC.

The process includes the following steps:
A) identifying a space CC surrounding the central voxel VXC and containing a group of peripheral voxels VXP (in FIG. 2, the reference VXP is graphically associated to a single voxel to simplify the drawing),
B) for each peripheral voxel VXP of the group in space CC, calculating a value proportional to the ratio or the difference between the density of the peripheral voxel VXP and the density of the central voxel VXC, thus obtaining a plurality of values,
C) calculating the maximum value and/or the minimum value and/or the average value and/or a statistical partitioning value of such values, thus obtaining a local indicator of inhomogeneity in the animal tissue in correspondence to the central voxel VXC.

The term "statistical partitioning value" means a value that partition a distribution or population of values; the terms "percentile" or "quantile" are used in statistics.

It should be noted that step C serves for globally assessing, i.e. by means of one or two or three numbers, a large plurality of values (the plurality may comprise from a few tenths to a few hundreds of value) and obtaining a "local indicator of inhomogeneity". In this respect, it may be useful to consider not just the maximum value but, for example, both the maximum and the minimum value or both the maximum and the minimum and the average value; these two or three numbers (or two or three equivalent numbers) may be combined by a suitable formula that produces a single "local indicator of inhomogeneity".

Based on the calculations made as indicated above, a 3-dimensional inhomogeneity map of the portion of animal tissue is obtained, corresponding to the starting 3-dimensional density map.

From the wide formulation given above it is understood that the method according to the present invention may be carried out in several different ways (a specific and especially advantageous exemplary embodiment will be described hereinafter).

At step B, for example, it is possible to contemplate a fixed or variable proportionality coefficient, or a nonlinear proportionality. For example, a variable proportionality coefficient may be used in case of difference and may correspond to the reciprocal of the distance between peripheral voxel and central voxel. For example, a nonlinear proportionality may correspond to the combination of linearity within a predetermined range and "saturation" (by such term meaning a limitation of the maximum value and/or of the minimum value of an operand and/or of the other operand and/or of the result) beyond such range.

Still at step B, according to the embodiment, the calculation (be it a difference or a ratio) may use the density of the central voxel or that of the peripheral voxel as a reference.

At step C, it may be useful to use more than one criterion for comparing different indicators of inhomogeneity.

At step A, the space may advantageously be selected in the shape of a sphere, but more advantageously in the shape of a "hollow sphere" (so as to exclude said central voxel and a neighborhood thereof), centered on the central voxel, as shown in FIG. 1: space CC is centered on voxel VXC and has the shape of a hollow sphere having smaller radius R1, larger radius R2 and thickness D (R2−R1). An extreme case of this choice (but less suitable for the lung tissue) corresponds to a spherical space, i.e. wherein R1=0 and D=R2.

The term "hollow sphere" herein means a sphere having a perfectly spherical inner cavity concentric to the outer surface; it is not excluded that other cavity shapes may be contemplated, substantially equivalent to the spherical cavity; it is worth noting that such volumes may consist, for example, of sets of cubes.

The Applicant has carried out several experiments with different values of R1, R2 and D.

The values used in these experiments have been selected based on a reference dimension R0, i.e. that of the radius of the medium lung acinus in different conditions of the human lung; in particular, the conditions considered are linked to the TLC [Total Lung Capacity]; the typical and average values of the radius of the medium lung acinus as a function of the lung inflation are shown hereinafter:

| Inflation | Radius (in mm) |
| --- | --- |
| 2 * TLC | 4.46 |
| TLC | 3.54 |
| TLC/2 | 2.81 |

-continued

| Inflation | Radius (in mm) |
|---|---|
| TLC/3 | 2.46 |
| TLC/4 | 2.23 |
| TLC/16 | 1.41 |
| TLC/64 | 0.89 |

It is also noted that the typical and average value of the radius of the medium lung acinus in conditions TLC/4 corresponds to about the typical and average value of the radius of the medium lung acinus in conditions FRC [Functional Residual Capacity].

While experiments have been carried out with all the RO values shown above (i.e. 0.89 mm to 4.46 mm), the RO values that appeared to be more suitable are those ranging between 2.23 mm (which corresponds to condition TLC/4 or FRC) and 3.54 mm (which corresponds to condition TLC).

The values in millimeters shown below are rounded to the tenth of millimeter and should in any case be understood as approximate.

As regards R1 (smaller radius of the hollow sphere), values in the range between 0.0 mm and 8.9 mm (i.e., in terms of radius of the acinus, 2.0*R0) were tested; considering then the above "suitable" range of R0, values in the range between 0.0 mm and 7.1 mm (i.e., in terms of radius of the acinus, 2.0*R0) were used but the best results were obtained in the range between 2.2 mm (i.e., in terms of radius of the acinus, 1.0*R0) and 5.3 mm (i.e., in terms of radius of the acinus, 1.5R0).

As regards R2 (larger radius of the hollow sphere), values in the range between 0.4 mm (i.e., in terms of radius of the acinus, 0.5*R0) and 13.4 mm (i.e., in terms of radius of the acinus, 3.0*R0) were tested; considering then the above "suitable" range of R0, values in the range between 1.1 mm (i.e., in terms of radius of the acinus, 0.5*R0) and 10.6 mm (i.e., in terms of radius of the acinus, 3.0*R0) were used but the best results were obtained in the range between 3.3 mm (i.e., in terms of radius of the acinus, 1.5*R0) and 8.8 mm (i.e., in terms of radius of the acinus, 2.5*R0).

As regards D (thickness of the hollow sphere), values in the range between 0.4 mm (i.e., in terms of radius of the acinus, 0.5*R0) and 4.5 mm (i.e., in terms of radius of the acinus, 1.0*R0) were tested; considering then the above "suitable" range of R0, values in the range between 1.1 mm (i.e., in terms of radius of the acinus, 0.5*R0) and 3.5 mm (i.e., in terms of radius of the acinus, 1.0*R0) were used.

Figure 2:
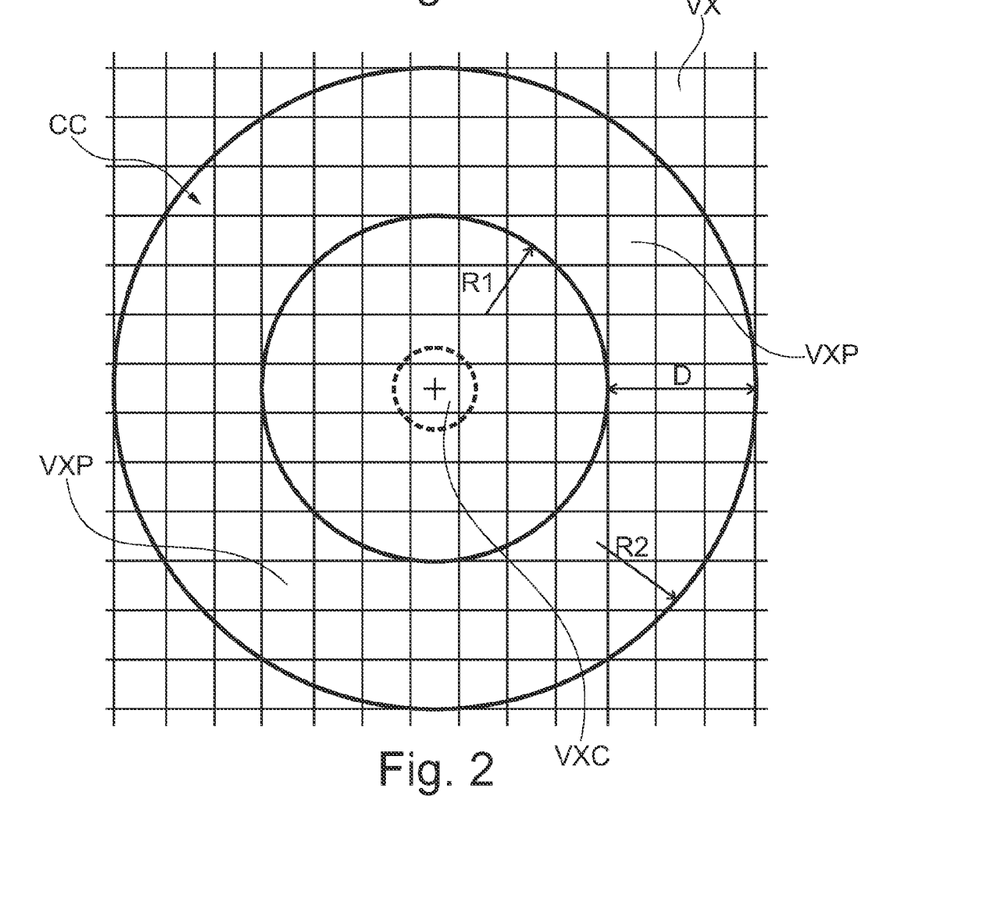
FIG. 2 shows a two-dimensional diagram (although the method according to the present invention operates threedimensionally) which serves for explaining an exemplary embodiment of the method according to the present invention.

In the exemplary embodiment of FIG. 2, space CC comprises some voxels entirely and other voxels partially only, i.e. those at the contour of space CC; in order to keep this into account, for example, it is possible to associate a weight (less than 1) thereto as a function of the percentage of overlapping with space CC. As an alternative, the method according to the present invention is carried out by means of a space formed by a 3-dimensional (and suitable) combination of voxels and which therefore is divided into squares.

As already said, for the method of the present invention to provide significant results it is necessary for the 3-dimensional density map used for determining the inhomogeneity to have a predetermined and narrow "spatial band" (in other words, with a predetermined and low maximum spatial frequency). More precisely, the maximum spatial frequency of the map must not be such as to show physiological inhomogeneities; for example, if a lung tissue were viewed at a very high resolution (which is currently not feasible with any kind of equipment), an alternation of air and biological material (cells) would be seen, but this is normal.

The Applicant has believed that the reference dimension for the lung tissue inhomogeneity assay is that of the lung acinus, indicated above with a R0; the typical radius thereof in conditions TLC ("Total Lung Capacity"=maximum inhalation) is about 3.5 mm and the average radius in conditions FRC ("Functional Residual Capacity"=end of the maximum exhalation) is about 2.2 mm; it is noted that during the natural breathing in a healthy individual, the lung cyclically and gradually goes from a maximum volume value to a minimum volume value (exhalation phase) and then from the minimum volume value to a maximum volume value (inhalation phase). Of course, for different tissues, the reference dimension may be very different (smaller or larger), according to the anatomical nature of the tissue.

Typically, the computed tomography equipment currently manufactured and marketed generate output 3-dimensional density maps with a resolution of 0.5-0.7 mm, and a corresponding "spatial band", i.e. the voxel of such maps is a cube having the side equal to 0.5-0.7 mm Thus, starting from such a high-resolution and large "spatial band" 3-dimensional map, it is necessary to spatially filter it by means of a spatial low-pass filter strongly attenuating spatial frequencies higher than a predetermined frequency corresponding to the reciprocal for a predetermined length ("characteristic filtering length").

The applicant has carried out several experiments using characteristic filtering lengths comprised in the range between 0.5 mm (corresponding to less than TLC/64) and 5.0 mm (corresponding to more than 2*TLC) and in particular, those corresponding to ¹/₆₄ of TLC, ¹/₁₆ of TLC, ¼ of TLC, ⅓ of TLC, ½ of TLC, once the TLC, twice the TLC; but the best results were obtained with lengths comprised in the range between 2.23 mm (which corresponds to condition TLC/4 or FRC) and 3.54 mm (which corresponds to condition TLC).

The transfer function of the spatial low-pass filter preferably is a decreasing monotone function, preferably a Gaussian function; as an alternative, the transfer function may for example be decreasing linear truncated at the annulment thereof or $\sin(f)/f$ truncated at the first annulment thereof or $\sin(f/n)/(f/n)*(\sin(f)/f)$ or $(\sin(f)/f)^2$ truncated at the first annulment thereof or $\cos^2(f)$ truncated at the first annulment thereof or $\sin(f)/(1-f2)$ truncated at the first annulment thereof or. In the case of Gaussian function, the strong attenuation may correspond, for example, to a predetermined attenuation that may range from a minimum value of about 70% (at a distance from the origin equal to 1 variance) to a maximum value of about 99.7% (at a distance from the origin equal to 3 variances). In the case of the other transfer functions, the strong attenuation may be equal to 100% at the first annulment thereof.

On the other hand, if starting from a 3-dimensional density map at suitable (i.e. sufficiently narrow) spatial band, the spatial low-pass filtering may not be required.

A specific and especially advantageous exemplary embodiment of the method according to the present invention contemplates the following steps (reference may again be made to FIG. 2):

A) calculating the "gas fraction" of the central voxel VXC,
B) identifying a space CC shaped as a hollow sphere (but not as a sphere) surrounding the central voxel VXC (the spherical cap is exactly centered on the central voxel VXC) and containing a group of peripheral voxels VXP,
C) for each peripheral voxel VXP of the group, calculating a value corresponding to the ratio between the "gas fraction" of the peripheral voxel VXP and the "gas fraction" of the central voxel VXC (i.e. making the calculation FGVXP/FGVXC), thus obtaining a plurality of values (RACC), D) calculating the maximum value among these values (RACC), thus obtaining a local indicator of inhomogeneity in the animal tissue in correspondence to the central voxel VXC.

The term "gas fraction" refers to the ratio of the electronic density expressed in Hounsfield or HU with number −1000; it is noted that the Hounsfield scale ranges from −1000 (air) to +1000 (compact bone) passing by 0 (water). Air is therefore considered as a relative reference and is associated to the "gas fraction" equal to 1 parameter; the lung tissue substantially behaves as water, i.e. it has an HU equal to about 0. Considering the physiological lung tissue, the density of its voxels may range from an absolute minimum value of about −1000 HU (air) to an absolute maximum value of about 0 HU (lung tissue cells) and the gas fraction thereof ranges from about 1 (air) to about 0 (lung tissue cells); therefore, the ratios calculated at step C, other observations lacking, range from very small values (for example 0.001 or even less) when in the central voxel there are lung tissue cells and in the peripheral voxel there is air at very large values (for example 1'000 or even more) when in the central voxel there is air and in the peripheral voxel there are lung tissue cells passing by values equal to about 1 when the central voxel is of the same type and therefore has the same density as the peripheral voxel.

A method equivalent to that just described can operate on the "tissue fraction" (=1−"gas fraction") rather than on the "gas fraction".

If every single step D is carefully considered, it is understood that using the maximum value of the ratios, this method shows inhomogeneities due to high density at the center and low density in the periphery. However, this method is able to show both possibilities of inhomogeneity in a portion of animal tissue since the maximum value calculation is repeated for all the voxels of the portion of animal tissue and therefore, an inhomogeneity due to low density at the center and high density in the periphery will show when the roles of central voxel and peripheral voxel are reversed; actually, the fact of considering only one type of inhomogeneity avoids the same situation from having to be considered twice.

Based on what said above, it is clear that other parameters may be used rather than the maximum value; in general, we may talk of "percentile" and mention, by way of an example only, the second quartile, or "median" (limit within which 50% of these values RACC fall) and the third quartile (limit within which 75% of these value RACC fall).

When the method according to the present invention (and also the specific exemplary embodiment just described) is implemented, it is suitable to perform some "limitation"/ "saturation" and/or "exclusion" operations on the initial data and/or on the intermediate results and/or on the final results; such operations are justified by computed processing reasons but more often, by biological and physiological observations; all of this is understood from the following examples.

For the purposes of the computed implementation of the method, it is advantageous to consider that the gas fraction of any voxel falls within a predetermined range; for example, such range goes from a minimum value, in particular 0.1, to a maximum value, in particular 1.0. For example, it is possible to first calculate the gas fraction and then limit or saturate it to a minimum and/or maximum value, if it exceeds; as an alternative, such "limitation" or "saturation" operation may be made on electronic density values of the voxel. Such "limitation" or "saturation" operation is not only justified by computed processing convenience but it also reflects biological and physiological observations; in fact, a lung tissue with gas percentage below 10% is considered as "non inflated" since some air remains trapped in the lung tissue by a collapse of the small bronchi.

For the purposes of the computed implementation of the method, it is advantageous to consider that the ratios calculated at step C fall within a predetermined range; for example, such range goes from a minimum value, in particular 0.1, to a maximum value, in particular 10.0. For example, it is possible to first calculate the ratio and then limit or saturate it to a minimum and/or maximum value, if it exceeds. Such "limitation" or "saturation" operation is not only justified by computed processing convenience but it also reflects biological and physiological observations; in fact, it would be quite unreasonable to assume that a lung tissue unit, although inflated, can have more than 10 times its basal gas.

The method described thus far (including the specific exemplary embodiment just described) provides a local indicator of inhomogeneity of the animal tissue, or better a plurality of local indicators corresponding to a plurality of values each for each voxel of the 3-dimensional map considered; for what described, the indicator according to the present invention has various alternatives, i.e. it may correspond to the maximum or to the average or to the minimum ratio.

A global indicator of inhomogeneity may be obtained from this local indicator of inhomogeneity. For example, an overall inhomogeneity level may be noted if for a predetermined percentage of the voxels of the portion of tissue considered, the local indicator of inhomogeneity exceeds a predetermined threshold.

For example, considering an application for mechanical ventilation, a hazard level may be noted if for a predetermined percentage of all the voxels of a portion of lung tissue (in particular, of the whole lung tissue of two lungs of an individual), the product between the transpulmonary pressure during a mechanical ventilation treatment and the local indicator of inhomogeneity raised to a predetermined power exceeds a predetermined threshold; this predetermined power is advantageously selected equal to $2/3$ (an exponent that makes a proportion of the area to the volume in an isomorphous expansion); this predetermined percentage is advantageously selected equal to about 5%; this predetermined threshold is advantageously selected equal to about 20 cm water; in this case, the most significant value of the "transpulmonary pressure" to be considered is the "plateau value". It is noted that the "transpulmonary pressure" is the force that stretches the lung both in the spontaneous and in the assisted breathing, and is the pressure difference between the pleural space and the air in the alveoli; in the positive pressure mechanical ventilation, a part of the pressure is used for stretching the lung and a part for expanding the lung; the force involved is only that required for expanding the chest; the "plateau value" is the pressure value registered during an inhalation end pause, i.e. in static conditions; the measurement in static conditions avoids having the forces needed to overcome the viscous resistances to be included in the calculation.

Figure 3:
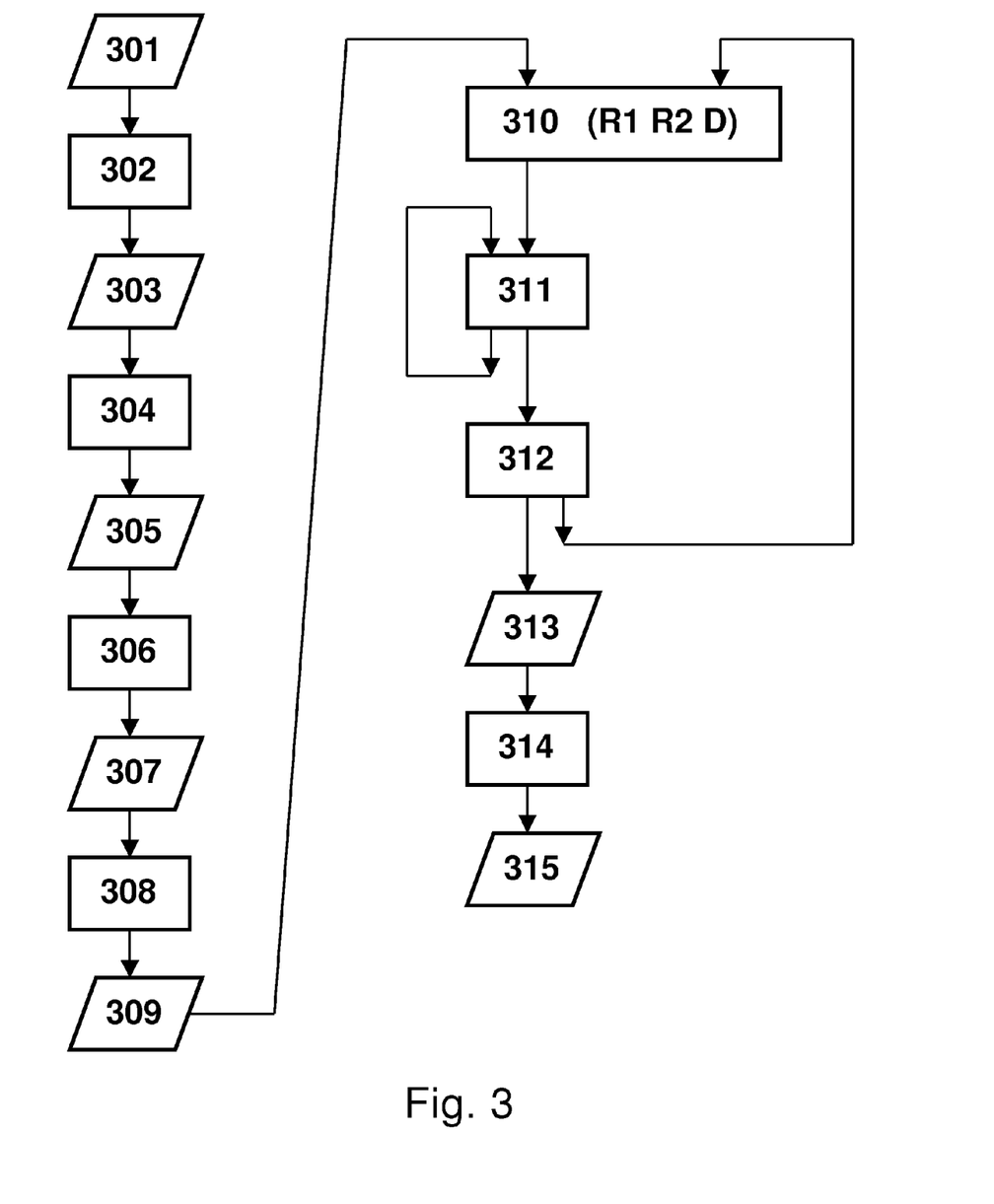
FIG. 3 shows a flow chart of an exemplary embodiment of the method according to the present invention.

FIG. 3 shows a flow chart of an exemplary embodiment of the method according to the present invention.

The method starts from high-resolution threedimensional density maps 301 having a large spatial frequency band generated by a commercial computed tomography equipment; of course, the method processes a single 3-dimensional map at a time. Then, there is a step 302 wherein an "original map" 301 is subjected to a "contouring" operation which serves for delimiting the tissue of the whole lung and thus to make the voxels outside the contour not be considered in the following processing; a "contoured map" 303 is thus generated.

Prior to the "contouring" operation of step 302, the "original map" 301 may be subjected to a "masking" operation, i.e. value HU of the "original map" 301 higher than, for example, 10 or 100 are excluded and therefore will not be considered in the following processing; such "masking" step is optional (thus, it is not shown in the flow chart of FIG. 3) and may be useful for preventing "artifacts" from being considered. For the reasons described above, there is then a step 304 of spatial filtering of the "contoured map" 303; a "filtered map" 305 is thus generated.

Then, there is a step 306 of "adjustment" of the density values of the "filtered map" 305. In such step, each of the density values of a "filtered map" is considered; if the value is less than −999, it is set equal to −999, if the value is more than −100, it is set equal to −100, otherwise the value is left unchanged; an "adjusted map" 307 is thus generated.

Then, there is a step 308 wherein a "map of gas fractions" 309 is generated.

The steps described below are those more strictly related to the determination of the inhomogeneity and which are carried out for each voxel in the "map of gas fractions" 309 considered as central voxel VXC.

There is a step 310 wherein a space CC around the central voxel is determined, based on parameters R1 and R2 or R1 and D or R2 and D, containing a plurality of peripheral voxels VXP.

There is a step 311 of calculation of the "gas fraction" ratios of each peripheral voxel VXP of space CC with the "gas fraction" of the central voxel VXC making the calculation FGVXP/FGVXC obtaining a plurality of values RACC.

There is a step 312 of calculation of the maximum one among the values of the plurality RACC.

A "map of maximum values" 313 is thus generated.

Finally, there may be a step 314 of "adjustment" of the maximum values of map 313. In such step, each of the maximum values of map 313 is considered; if the value is less than 1, it is set equal to 1, otherwise the value is left unchanged; a "map of adjusted maximum values" 315 is thus generated which, according to the present invention, is used as "map of local inhomogeneity".

The method just described lends itself to changes and/or additions.

For example, as an alternative or in addition to step 308 of generation of the "map of gas fractions" 309, there may be a step of generation of a map of "tissue fractions" and/or "gradients".

For example, as an alternative or in addition to step 312 of calculation of the maximum values and generation of the relative map 313, there may be a step of calculation of one or more predetermined "percentiles" (or other values resulting from statistical partitionings) and of generation of a relative map.

The method according to the present invention lends itself to be implemented by a computer program; this will then comprise code portions adapted to carry out the steps of the method when they are executed by a computer.

Such program may be installed on and executed by a computed tomography equipment already manufactured and operating, for example, in a hospital; in fact, such type of equipment always integrates a computer with various programs installed and working; therefore, this may be a further program for obtaining further information about the examined individual.

The method according to the present invention may be implemented in a computed tomography equipment and thus create a new and useful apparatus. Such equipment comprises specific means adapted to implement the method, in particular internal or external memory means storing a computer program as indicated above.

The invention claimed is:

1. A method for applying mechanical ventilation to a lung tissue of an animal, the method comprising:
providing a 3-dimensional density map of a portion of the lung tissue, said 3-dimensional density map being obtained by means of computed tomography and being formed by a plurality of voxels, the method further comprising, for each voxel of said 3-dimensional map considered in turn as a central voxel;
identifying a space surrounding said central voxel and containing a group of peripheral voxels,
for each peripheral voxel of said group, calculating a value proportional to the ratio or the difference between the density of said peripheral voxel and the density of said central voxel, thus obtaining a plurality of values, and
calculating the maximum value and/or the minimum value and/or the average value and/or a statistical partitioning value of said values, thus obtaining a local indicator of inhomogeneity of said portion of animal lung tissue in correspondence to said central voxel; and
applying mechanical ventilation to the lung tissue of the animal based on the obtained local indicator of inhomogeneity.

2. The method according to claim 1, wherein said space is a sphere, preferably a hollow sphere, centered on said central voxel.

3. The method according to claim 2, wherein the smaller radius of said sphere is comprised between 0.0 mm and 7.1 mm, in particular between 2.2 mm and 5.3 mm.

4. The method according to claim 2, wherein the larger radius of said sphere is comprised between 1.1 mm and 10.6 mm, in particular between 3.3 mm and 8.8 mm.

5. The method according to claim 2, wherein the thickness of said sphere is comprised between 1.1 mm and 3.5 mm.

6. The method according to claim 1, wherein said 3-dimensional density map derives from a 3-dimensional original map produced by a computed tomography equipment and then spatially filtered by means of a spatial low-pass filter strongly attenuating spatial frequencies higher than a predetermined frequency corresponding to the reciprocal for a predetermined length.

7. The method according to claim 1, wherein, for each voxel of said 3-dimensional density map, considered in turn as the central voxel, the following steps are carried out: A) calculating the "gas fraction" of said central voxel, B) identifying a space shaped as a hollow sphere surrounding said central voxel and containing a group of peripheral voxels, C) for each peripheral voxel of said group, calculating a value corresponding to the ratio between the "gas fraction" of said peripheral voxel and the "gas fraction" of said central voxel, thus obtaining a plurality of values, D) calculating the maximum of said values, thus obtaining a local indicator of inhomogeneity of said portion of lung tissue in correspondence to said central voxel.

8. The method according to claim 1, wherein said portion of lung tissue corresponds to a whole lung.

9. The method according to claim 1, wherein a global indicator of inhomogeneity is obtained by said local indicator of inhomogeneity of all voxels of said portion of lung tissue.

* * * * *